United States Patent [19]

Kurihara

[11] Patent Number: 5,705,738

[45] Date of Patent: Jan. 6, 1998

[54] PRECISE SHEAR-STRESS MEASUREMENT APPARATUS

[75] Inventor: Kazue Kurihara, Aichi, Japan

[73] Assignee: Japan Science And Technology Corporation, Saitama, Japan

[21] Appl. No.: 784,704

[22] Filed: Jan. 16, 1997

[51] Int. Cl.⁶ .................................................. G01N 11/10
[52] U.S. Cl. ........................................ 73/54.39; 73/54.01
[58] Field of Search ........................... 73/54.01, 54.02, 73/54.22, 54.23, 54.39, 54.41, 841, 847

[56] References Cited

U.S. PATENT DOCUMENTS

| | | | |
|---|---|---|---|
| 4,896,339 | 1/1990 | Fukumoto | 73/81 |
| 5,094,100 | 3/1992 | Dealy et al. | 73/54.01 |
| 5,163,317 | 11/1992 | Ono et al. | 73/54.39 |

*Primary Examiner*—Richard Chilcot
*Assistant Examiner*—Max H. Noori
*Attorney, Agent, or Firm*—Flehr Hohbach Test Albritton & Herbert LLP

[57] ABSTRACT

A precise shear-stress measurement apparatus includes a spring disposed perpendicularly to a sample surface, and a cylindrical piezoelectric element disposed perpendicularly to the sample surface and connected to the spring. The piezoelectric element is circumferentially divided into a plurality of pieces. The apparatus further includes a circuit for driving the piezoelectric element, a capacitance-type displacement gauge for detecting a horizontal displacement of the spring, and a battery for driving the displacement gauge. This reduces noise from an electric system, thereby making it possible to precisely measure even rheology motion in a very small space on the order of nanometers.

9 Claims, 7 Drawing Sheets

F I G. 3
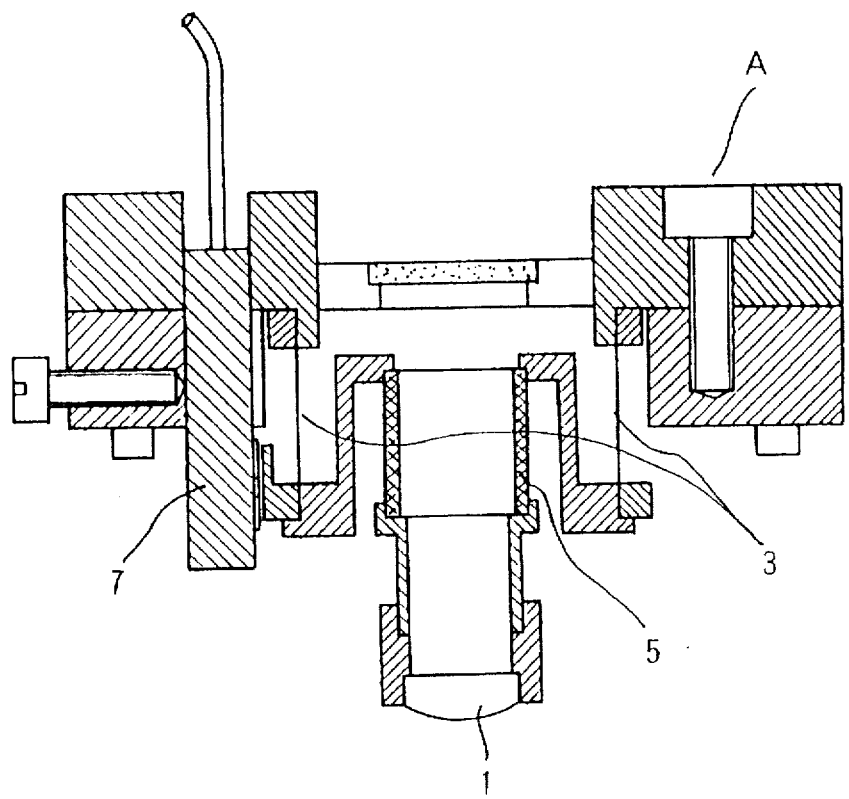
F I G. 5
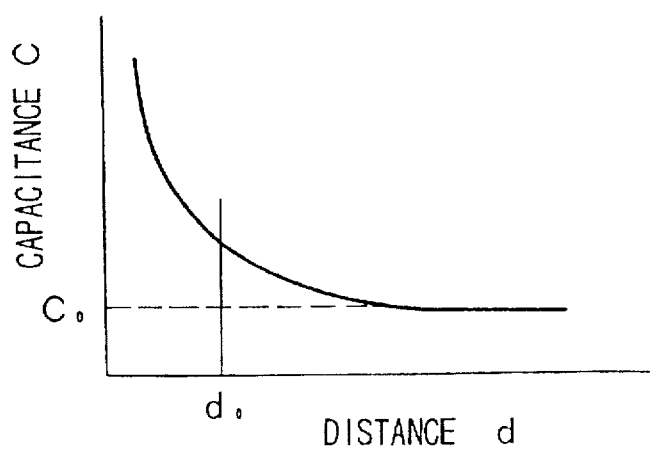

1

PRECISE SHEAR-STRESS MEASUREMENT APPARATUS

BACKGROUND OF THE INVENTION

1. Field of the Invention

The present invention relates to a precise shear-stress measurement apparatus for measuring lubricity or friction of a sample surface, deformation of a polymer absorption layer, or formation and collapse of a structure in liquid or liquid crystal confined in a narrow space, through measurement of shear-stress to a precision on the order of nanometers.

2. Description of the Related Art

Conventionally, in order to carry out studies on lubricity and friction of a surface, a so-called "shear-stress measurement apparatus" has been developed. In the shear-stress measurement apparatus, the relative position between two surfaces is periodically varied in a horizontal direction while the distance and mutual action between the surfaces are accurately controlled, and stress is measured as a function of slippage.

FIG. 1 shows such a conventional shear-stress measurement apparatus.

In FIG. 1, numeral 101 denotes a sample in the form of liquid or liquid crystal confined in a narrow space. In this case, the characteristics of the sample 101 are examined. Numerals 102 and 104 denote blocks having sample surfaces. The block 102 is driven by a piezoelectric element or a like element, so that the block 102 precisely moves parallel to the sample surface of the block 104. Numeral 103 denotes a pair of springs for measurement of shear-stress, and numeral 105 denotes a measurement system with a spring for measuring a surface force. In this apparatus, the distance D between the sample surfaces of the blocks 102 and 104 is set to a predetermined value. The apparatus may be operated without the sample 101, in which case, the sample surfaces of the blocks 102 and 104 are brought into direct contact with each other and shear is caused therebetween.

Israelachvili, et al. have proposed a system in which a variable speed motor is used as a mechanism for accurately moving one surface parallel to the other surface, and a stainless steel spring and a strain gauge are used for measurement of surface stress (see *Science*, 240, 189, (1988)).

The system measures a stress that acts on a surface, which is moved over a distance of a few tens of micrometers during a period on the order of "minutes." The system can perform measurement in a wide range from $10^{-6}$ to $10^{-3}$N.

However, this system is not suitable for measurement of small stress or quick changes in shear.

Further, Klein, et al. have proposed a system in which a piezoelectric element is used as a mechanism for precisely moving one surface parallel to the other surface, and a stainless steel spring and an air-gap capacitance method are used for measurement of surface stress (see *Nature*, 352, 143, (1991)). This system can measure a stress equal to or greater than $10^{-7}$N in a state in which a surface is very precisely moved in a horizontal direction. The surface can be moved over a distance of 3 micrometers with a positional precision of ±0.1 nm.

However, the system cannot measure a smaller stress with higher precision because of vibration and noise from the electric system.

SUMMARY OF THE INVENTION

An object of the present invention is to solve the above-mentioned problems, and to provide a precise shear-stress measurement apparatus that uses, as a power source, a battery that is isolated from the external environment so as to reduce noise from the electric system, thereby making it possible to measure, to a precision on the order of nanometers, even rheology motion in a very small space.

In order to attain the above-described object, the present invention provides a precise shear-stress measurement apparatus which includes a spring disposed perpendicularly to a sample surface, and a cylindrical piezoelectric element disposed perpendicularly to the sample surface and connected to the spring. The piezoelectric element is circumferentially divided into a plurality of pieces. The apparatus further includes a circuit for driving the piezoelectric element, a capacitance-type displacement gauge for detecting a horizontal displacement of the spring, and a battery for driving the displacement gauge.

Since a battery isolated from the external environment is used as a power source, noise from external electric wire and peripheral devices can be reduced. This noise reduction effect becomes especially remarkable when studies are carried out on rheology motion in a very small space on the order of nanometers.

In shear-stress measurement, there is oftentimes expected generation of a phase shift between the waveform of voltage applied to the piezoelectric element (which is a function that indicates movement of a surface) and an output representing a measured shear stress. When such a phase shift is generated, it become difficult to use a lock-in amplifier that is generally used to reduce noise. Reduction of noise in the output signal is essentially important. However, in the case where the output signal indicating a measured shear stress has the same waveform and phase as those of the voltage applied to the piezoelectric element, use of a lock-in amplifier is effective.

In the shear-stress measurement apparatus of the present invention, the piezoelectric element preferably has a four-segment structure having a common electrode and at least two drive electrodes, and first and second voltages each having a triangular waveform are supplied to the drive electrodes, the first and second voltages having a phase difference of 180° therebetween.

This simple structure makes it possible to drive a surface in, for example, the X-direction within a range of ±27 nm at a frequency of 30 Hz (1.6 µm/sec), and a frictional force of $3\times10^{-6}$N can be obtained at that time.

Preferably, a member that provides the sample surface has a lens-like shape and is replaceable, and the member is held by a pair of springs disposed perpendicular to the sample surface and is moved horizontally by the piezoelectric element at a constant speed.

In this case, setting for shear-stress measurement can be easily performed for various kinds of samples.

The sample surface may be a surface of a solid material such as glass or mica, or a chemically modified surface of the solid material.

The capacitance-type displacement gauge is preferably provided with a lock-in amplifier.

In this case, measurement precision can be increased to about ±0.3 nm.

The present invention also provides a precise shear-stress measurement apparatus comprising a spring disposed perpendicularly to a sample surface; a cylindrical piezoelectric element disposed perpendicularly to the sample surface and connected to the spring, the piezoelectric element being circumferentially divided into a plurality of pieces; means for driving the piezoelectric element; and a capacitance-type displacement gauge for detecting a horizontal displacement of the spring; wherein the measurement apparatus is assembled as an exchangeable unit. In this case, the precise shear-stress measurement apparatus is immersed into a liquid in a sealed container.

In this case, it becomes possible to measure a structure or the like in liquid confined in a narrow space between a pair of surfaces.

Especially, the shear-stress measurement apparatus can be built, as an exchangeable unit, into a surface-force measurement apparatus (see FIG. 10) which measures a force in the vertical direction. This makes it possible to change one of sample surfaces, i.e., makes it possible to replace the sample section 35 in FIG. 10 with the above-described shear-stress measurement apparatus, thus increasing reliability of measurement. In addition, the vertical distance and mutual action between the two surfaces can be easily set.

Preferably, the surface-force measurement apparatus includes means for measuring the distance between a pair of sample surfaces and means for changing the distance between the pair of sample surfaces.

With this structure, it becomes possible to measure shear-stress while the distance between two surfaces and a vertical force acting on the surfaces are controlled in a variable manner. Preferably, the distance between two surfaces is determined through measurement of interference fringes using white light (see FIG. 10).

BRIEF DESCRIPTION OF THE DRAWINGS

FIG. 3 is a sectional view showing an assembled state of the precise shear-stress measurement apparatus;

FIG. 5 is an explanatory view showing displacement measurement by a capacitance method employed in the embodiment of the present invention;

DESCRIPTION OF THE PREFERRED EMBODIMENTS

Embodiments of the present invention will now be described with reference to the drawings.

First, a description will be given of an embodiment in which a frictional force between a glass surface and a mica surface is measured.

Figure 1:
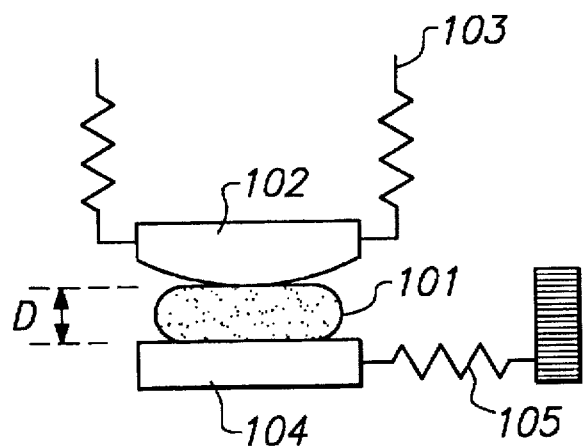
FIG. 1 is a view showing the structure of a conventional precise shear-stress measurement apparatus.
Figure 2:
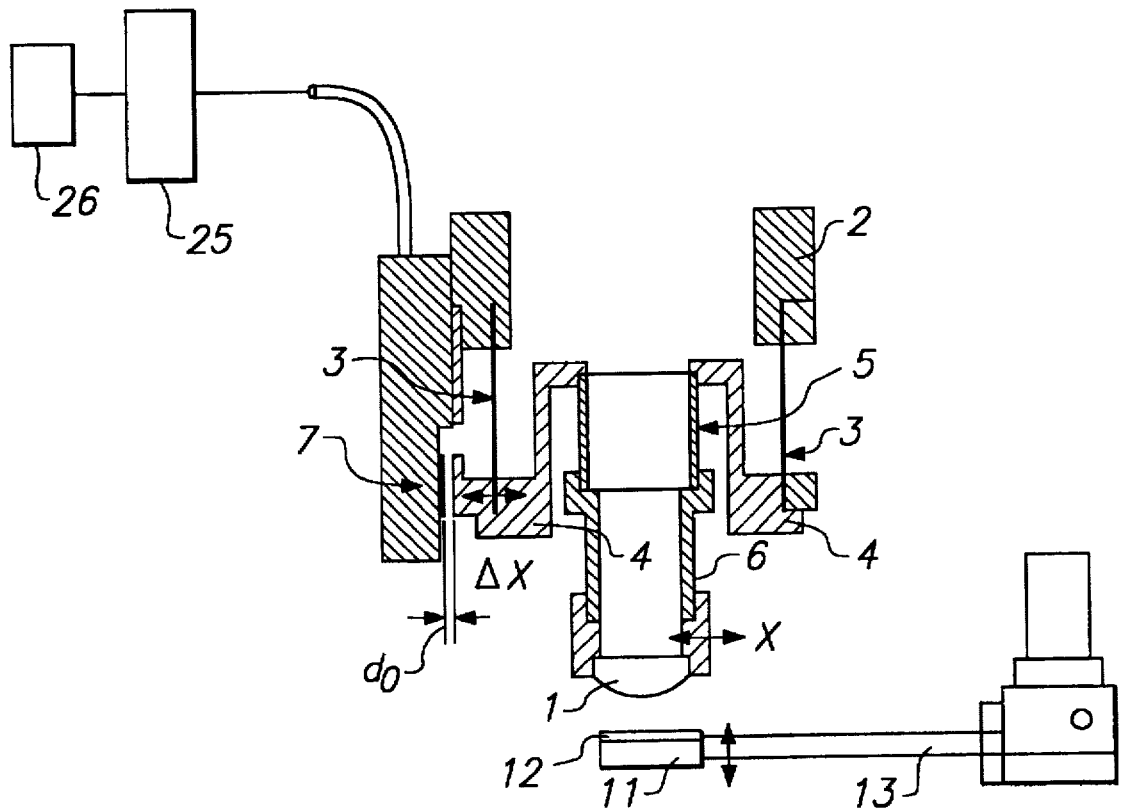
FIG. 2 is a sectional view of a precise shear-stress measurement apparatus showing an embodiment of the present invention.

In FIGS. 2 and 3, numeral 1 denotes a silica lens, numeral 2 denotes a stationary portion, numeral 3 denotes a pair of springs disposed perpendicularly to the surface of the silica lens. 1 to be measured, and numeral 4 denotes connection members. The inner edge portion of the connection member 4 is bent upward. Numeral 5 denotes a piezoelectric element (four-segment cylindrical piezoelectric element; Morgon, PZT8-8031-5H). The piezoelectric element 5 is fixed to the inner edge portion of the connection member 4 and extends in a direction perpendicular to the silica lens 1. Numeral 6 denotes a holding member that extends downward from the piezoelectric element 5 and serves to hold the silica lens 1, and numeral 7 denotes a displacement gauge probe which detects the displacement of the connection members 4. Numeral 11 denotes a silica lens, numeral 12 is a sheet of mica fixed to the surface of the silica lens 11, and numeral 13 denotes a spring that forms part of a measuring system for measuring a vertical force (force in the Z-axis direction).

Figure 10:
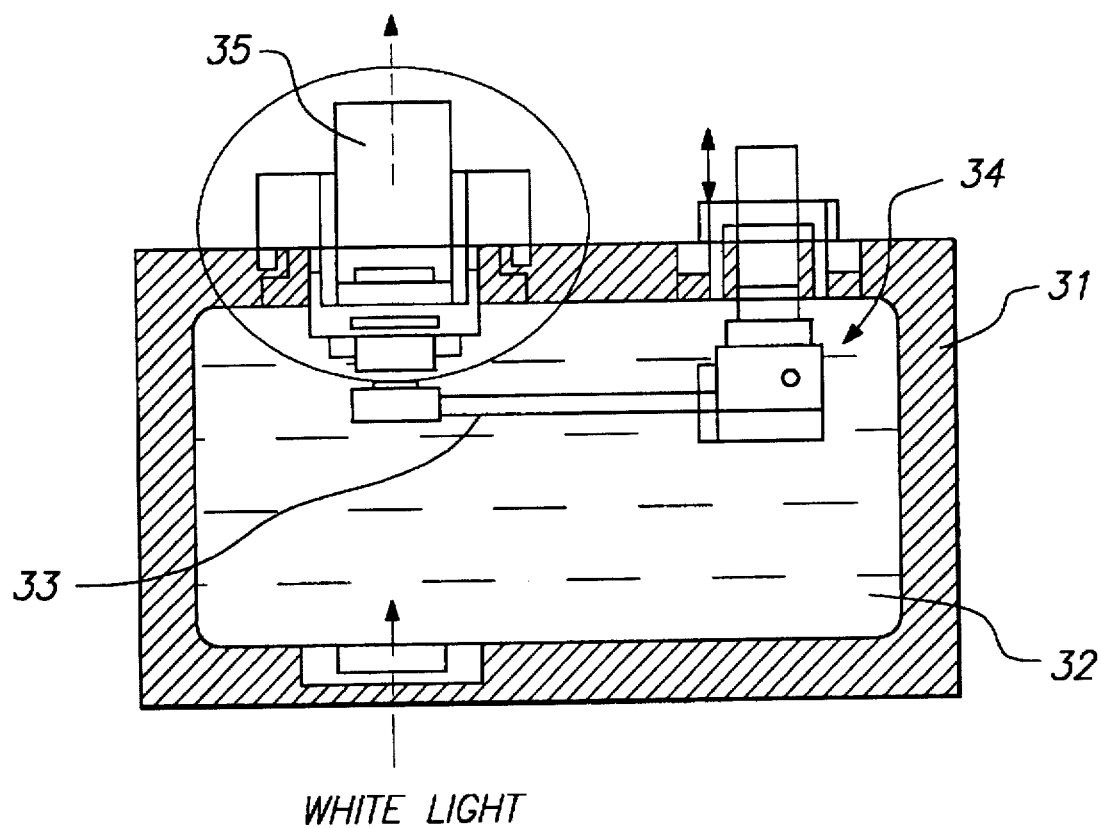
FIG. 10 is a sectional view of a surface-force measurement apparatus into which the precise shear-stress measurement apparatus according to the embodiment of the present invention is to be incorporated.

The piezoelectric element tube (sample section) 35 of a surface-force measurement apparatus shown in FIG. 10 can be replaced with the shear-stress measurement apparatus shown in FIG. 3, and when this is done, the shear-stress measurement apparatus is fixed to the top plate 31 of the surface-force measurement apparatus.

Figure 4:
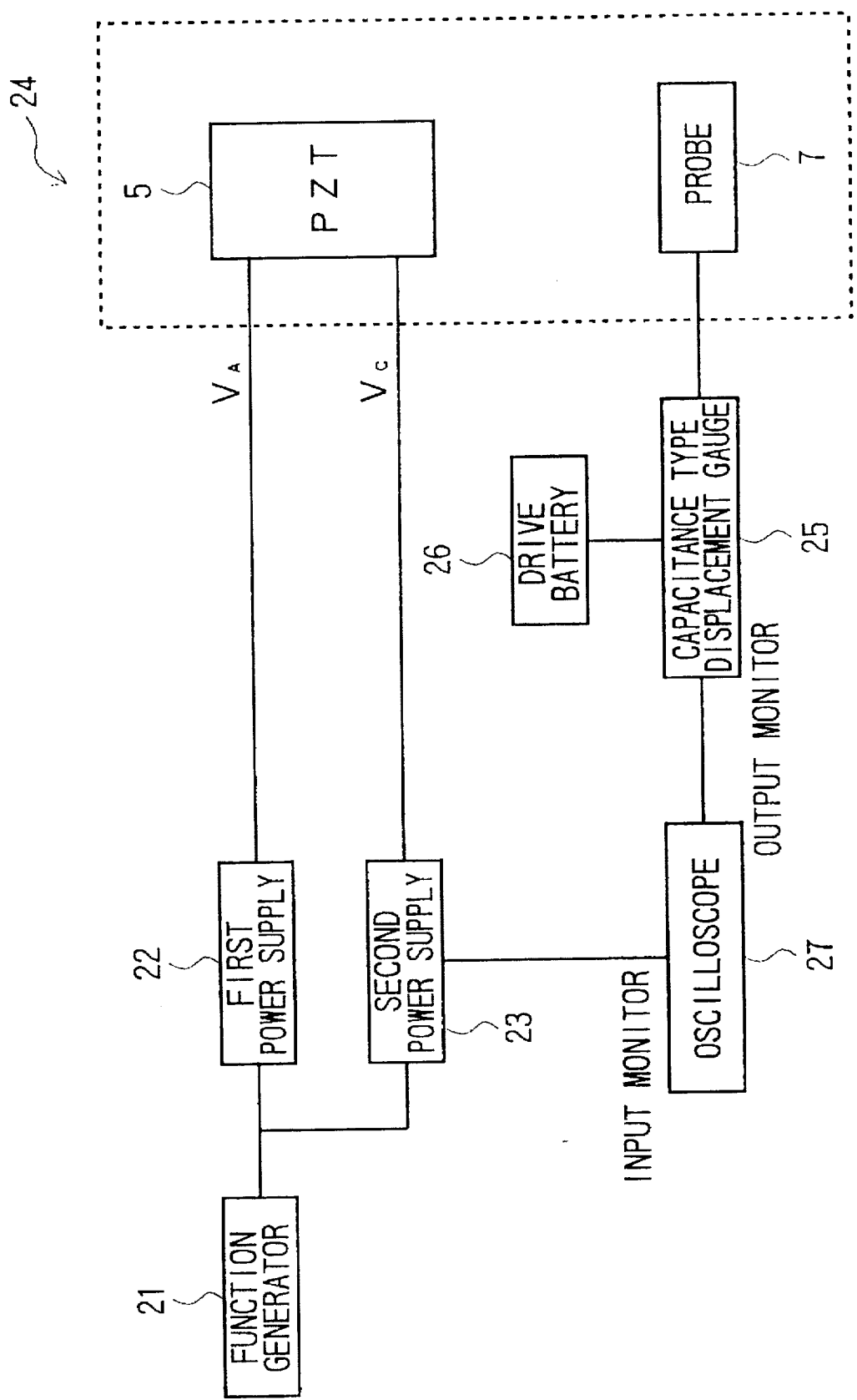
FIG. 4 is a block diagram of the precise shear-stress measurement apparatus according to the embodiment of the present invention.
Figure 7:
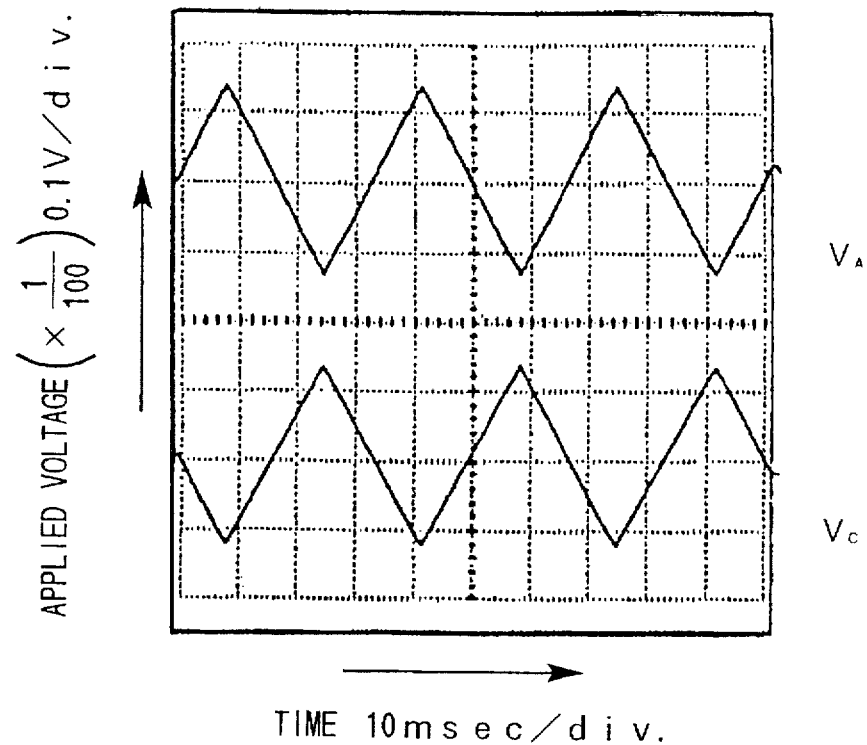
FIG. 7 is a graph showing the waveforms of voltages applied to the piezoelectric element.

In FIG. 4, numeral 21 denotes a function generator, numeral 22 denotes a first power supply for supplying voltage $V_A$ (see the upper waveform in FIG. 7), and numeral 23 denotes a second power supply for supplying voltage $V_C$ (see the lower waveform in FIG. 7). Numeral 24 denotes a shear-stress measurement system, numeral 25 denotes a capacitance-type displacement gauge connected to the displacement gauge probe 7, numeral 26 denotes a battery, such as a nickel-cadmium battery, that serves as a power source for the capacitance-type displacement gauge 25, and numeral 27 denotes an oscilloscope. The oscilloscope 27 simultaneously measures, as a function of time, the output of the capacitance-type displacement gauge 25 and voltages which are output from the power supplies 22 and 23 to the piezoelectric element 5.

Next, a description will be given of displacement measurement in accordance with the capacitance method. In this method, the distance D between the displacement gauge probe 7 and a surface opposite to the probe 7 is measured based on the fact that the capacitance between the displacement gauge probe 7 and the surface opposite to the probe 7 varies in inverse proportion to the distance D (see FIG. 2).

That is, high-frequency voltage is applied to the gap between the displacement gauge probe 7 and the surface through the electrode of the displacement gauge probe 7, and current (AC current) flowing through the gap at that time is measured. Actually, this current is converted into a voltage signal by an appropriate circuit and the voltage signal is output. The capacitance C thus measured is the sum of the capacitance $C_s$ of the space between the displacement gauge probe 7 and the surface opposite to the probe 7, and a capacitance $C_o$ of other portions such as the circuit portion of the measurement apparatus. That is, the measured capacitance C is expressed as follows:

$$C = C_s + C_o = (KA/d) + C_o$$

wherein K is a dielectric constant, and A is an area of the probe.

In the current measurement, it is necessary to measure a very small displacement on the order of nanometers from a position that is separated from the probe 7 by a predetermined distance $d_o$, as shown in FIG. 5.

As described above, high-frequency voltage is applied to the probe 7. In such a case, it is effective to reduce electrical fluctuation through use of a battery as a power source.

This stabilizes the capacitance $C_o$ whose origin is unknown, thereby making it possible to carry out more precise measurement.

The combination of glass and mica surfaces can be freely replaced with other sample surfaces. Also, the measurement apparatus can be designed as an exchangeable unit that can be built in the ordinary surface-force measurement apparatus shown in FIG. 10. In the unit, a measurement surface is held by two springs 3 disposed perpendicularly to the measurement surface, and the measurement surface is moved horizontally at a constant speed by the piezoelectric element 5.

Figure 6:
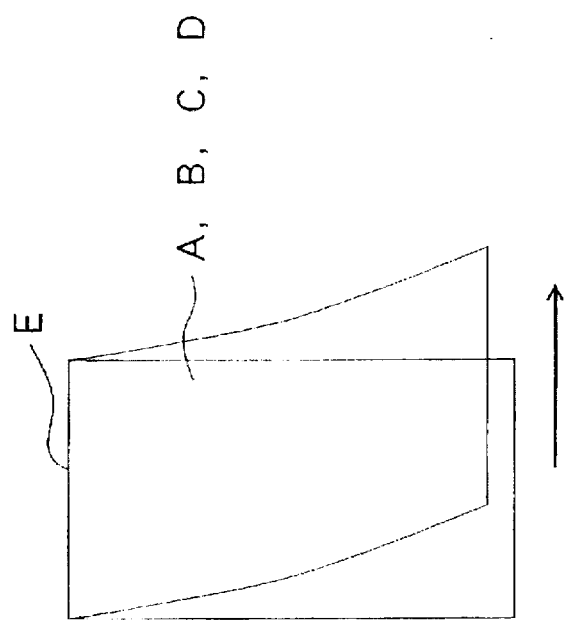
FIGS. 6A and 6B are views showing a piezoelectric element that is used in the embodiment of the present invention so as to generate shear stress.
Figure 6:
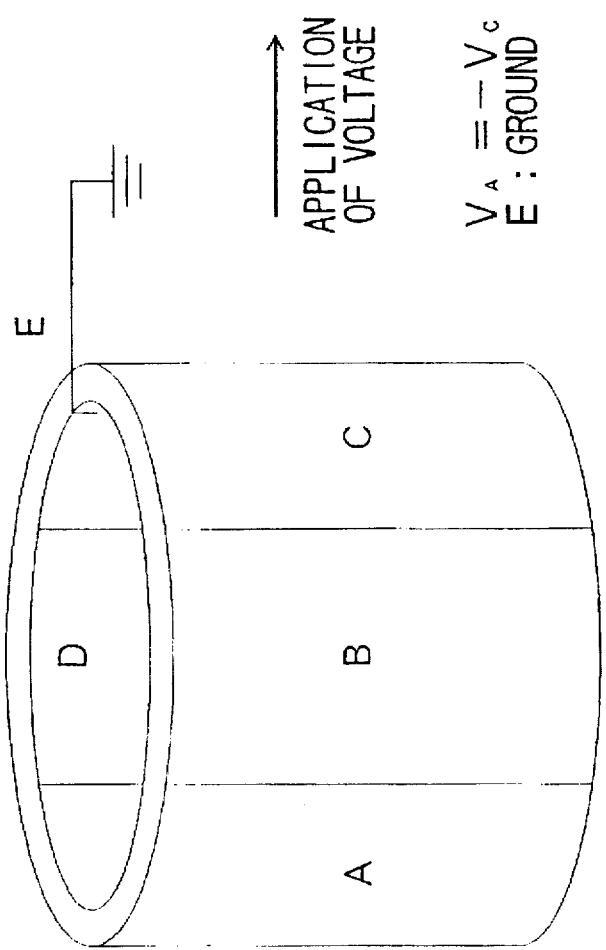

As shown in FIG. 6A, the piezoelectric element 5 is a cylindrical piezoelectric element having four segmented outer electrodes (A, B, C, and D) and an inner common electrode that is connected to the ground (E). Two voltages $V_A$ and $V_C$ each having a triangular waveform as shown in FIG. 7 are respectively supplied to the outer electrodes A and C of the piezoelectric element 5. Since a phase difference of 180° exists between the two voltages $V_A$ and $V_C$, the sample surface is moved in the X-axis direction (208 nm/100 V, maximum displacement: a few micrometers) at a frequency up to a few hundred Hz.

As shown in FIG. 4, signals from the function generator 21 are amplified by the power supplies (ENP-2001A, product of Echo Electric, Co.) 22 and 23. A force $F_1$ in the horizontal direction is measured as a horizontal displacement ($\Delta X$) of the springs 3 that hold the sample surface. The horizontal displacement of the springs 3 is measured through use of a displacement gauge utilizing an air-gap capacitance method (MICROSENSE non-contact type micro displacement gauge 3401HR-01, product of Nippon ADE). The force $F_1$ is calculated by the following equation:

$$F_1 = K_1 \cdot \Delta X$$

wherein $K_1$ is a spring constant ($K_1 \approx 320$ N/m).

As described later, the precision in measuring the $\Delta X$ is ±1 nm. When the drive voltages have triangular waveforms, the upper limit of the frequency of the drive voltages is a few hundred Hz. However, the apparatus cannot be operated in the vicinity of 100 Hz, which is the resonant frequency of the apparatus. The resonant frequency varies depending on the design of the holding member and other members, as well as a spring constant employed.

A sheet of mica 12 that is smooth at the level of molecules is fixed onto the silica lens 11 having a cylindrical shape (curvature: R—20 mm) so as to provide a measurement surface or sample surface. The two lenses are disposed such that their axes intersect perpendicular to each other. One of the surfaces is held by one end of the spring ($K_2 \approx 100$ N/m) 13. The distance between the surfaces is measured by an equal chromatic order interference method, and a force in the vertical direction ($F = K \Delta z$) is obtained from the displacement ($\Delta z$) of the spring 13.

Instead of the above-described triangular waves, sinusoidal waves, rectangular waves, or other waves may be used.

Measurement Example (1) Spring Displacement:

The displacement of the springs 3 was measured using the air-gap capacitance method. When $\Delta X$ was measured to a precision of ±1 nm, noise from the power supply could not be ignored. Therefore, in order to obtain a stable response, the power supply of the capacitance-type displacement gauge 25 was replaced with a battery serving as a DC power supply 26. Also, it was confirmed that use of a lock-in amplifier made it possible to carry out measurement to a precision of about ±0.3 nm.

However, the measurement described in the following section (2) was performed without using a lock-in amplifier.

(2) Friction between glass surface and mica surface:

A glass surface and a mica surface were brought into contact with each other, and the glass surface was repeatedly moved in the X-axis direction at 30 Hz. Stress due to friction at that time was examined.

Figure 8:
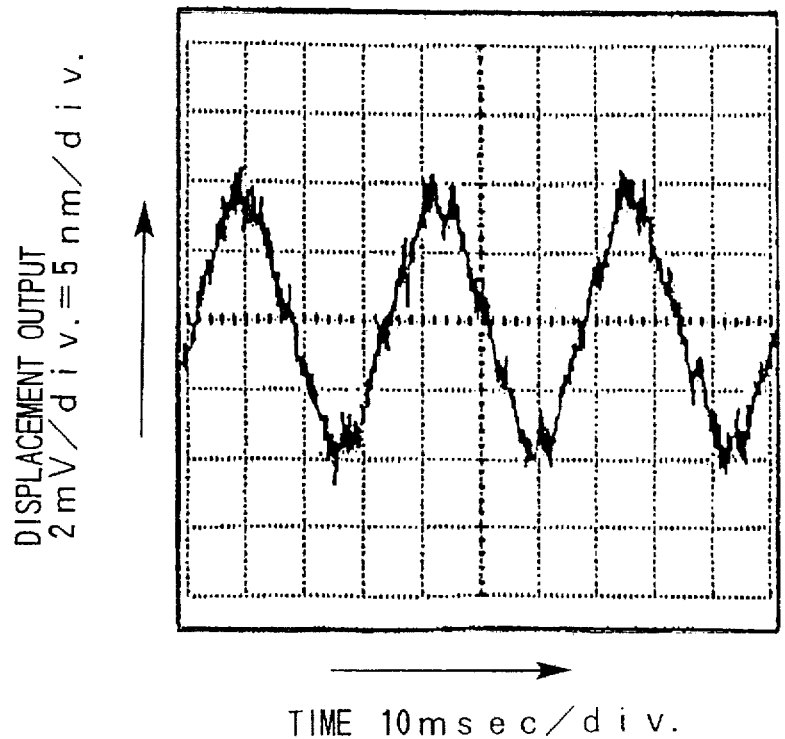
FIG. 8 is a graph showing output of a displacement gauge.

FIG. 7 shows voltages (×1/100) input to the piezoelectric element, and FIG. 8 shows a monitor signal representing the displacement $\Delta X$ of the spring at that time (2 mV/div corresponds to a displacement of 5 nm/div). When the two surfaces were separated from each other, $\Delta X$ became almost zero. Calculation based on these data indicated that the frictional force was $3 \times 10^{-6}$ N when the surface was moved at a speed of 1.6 μm/sec (actual moving distance: ±2.7 nm) at 30 Hz.

As described above, since battery drive was employed so as to reduce noise from the power supply, noise reduction was actually attained. This noise reduction effect becomes remarkable when rheology motion is studied on periodical movement of a surface within a very small space on the order of nanometers.

Figure 9A:
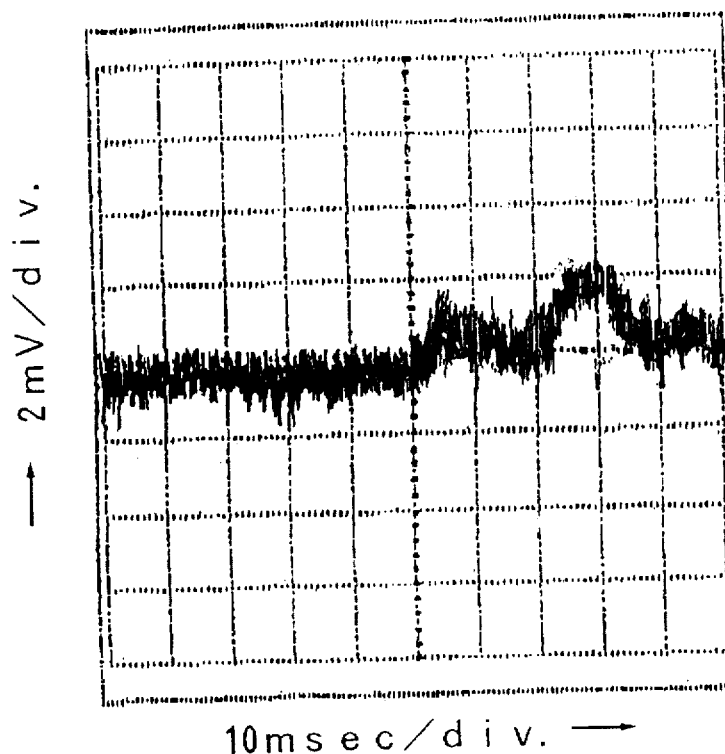
FIG. 9A is a graph showing the instability/stability in distance measurement in accordance with a capacitance method for the case of AC drive.
Figure 9B:
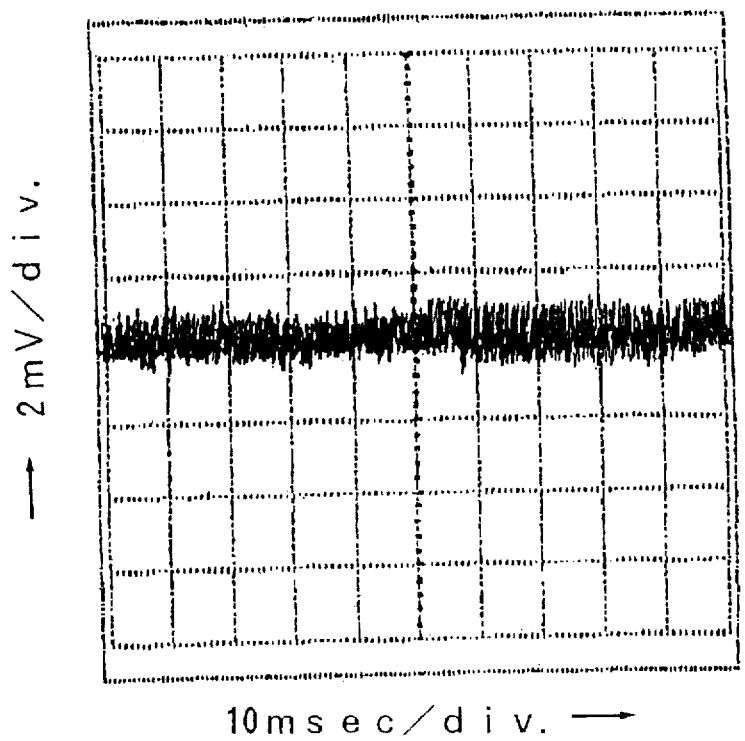
FIG. 9B is a graph showing the stability in distance measurement in accordance with a capacitance method for the case of battery drive.

The graph of FIG. 9A shows displacement of the spring in the case of AC drive, while the graph of FIG. 9B shows displacement of the spring in the case of DC drive. In each of these graphs, the vertical axis indicates the output of the displacement gauge (2 mV/div) and the horizontal axis indicates time (10 msec/div).

As is apparent from these graphs, in the case of DC drive shown in FIG. 9B, displacement of the springs 3 was more stable as compared to the case of AC drive shown in FIG. 9A.

The increased stability of displacement of the springs 3 attributable to DC drive greatly increases the precision in shear-stress measurement.

In the shear-stress measurement apparatus according to the present invention, the sensitivity of stress detection is $10^{-7}$ N. However, the sensitivity can be increased further through employment of a low-pass filter, a high-pass filter, and the like. Especially, the shear-stress measurement apparatus according to the present invention has an advantage of not being affected by long-term electrical fluctuation.

FIG. 10 is a sectional view of a surface-force measurement apparatus into which the precise shear-stress measurement apparatus according to the embodiment of the present invention is incorporated.

In FIG. 10, numeral 31 denotes a sealed container, numeral 32 denotes an aqueous solution, numeral 33 denotes a spring, numeral 34 denotes a Z-axis direction drive section that supports the spring 33, and numeral 35 denotes a sample section into which the above-described exchangeable unit is built.

The surface-force measuring apparatus having the above-described structure can measure the structure in liquid confined in a narrow space between a pair of surfaces.

Since the shear-stress measurement apparatus (X-axis direction displacement measurement section) can be easily exchanged with any other unit, reliability of measurement can be increased, and setting operation therefor can be facilitated.

In the surface-force measuring apparatus, the distance between two surfaces may be determined through measurement of interference fringes using white light, and the distance can be changed through movement of the spring 33 using the Z-axis direction drive section 34. Therefore, it becomes possible to measure shear-stress while the distance between two surfaces and a vertical force acting on the surfaces are controlled in a variable manner.

Instead of paired glass and mica, various kinds of paired samples may be set. For example, a surface of a solid material such as glass or mica may be contacted with a chemically modified surface of the solid material. Also, a sample in the form of liquid may be interposed between a pair of surfaces. Therefore, paired surfaces are not necessarily required to be in mutual contact.

Although the container 10 is filled with a solution in the above-described embodiment, it is unnecessary in some cases to fill the container 10 with a solution.

In shear-stress measurement, there is oftentimes expected generation of a phase shift between the waveform of voltage applied to the piezoelectric element (which is a function that indicates movement of a surface) and an output representing a measured shear stress. When such a phase shift is generated, it become difficult to use a lock-in amplifier that is generally used to reduce noise. Reduction of noise in the output signal is essentially important. However, in the case where the output signal indicating a measured shear stress has the same waveform and phase as those of the voltage applied to the piezoelectric element, use of a lock-in amplifier is effective.

The present invention is not limited to the above-described embodiments. Numerous modifications and variations of the present invention are possible in light of the spirit of the present invention and they are not excluded from the scope of the present invention.

What is claimed is:

1. A precise shear-stress measurement apparatus comprising:

(a) a spring disposed perpendicularly to a sample surface;

(b) a cylindrical piezoelectric element disposed perpendicularly to said sample surface and connected to said spring, said piezoelectric element being circumferentially divided into a plurality of pieces;

(c) means for driving said piezoelectric element;

(d) a capacitance-type displacement gauge for detecting a horizontal displacement of said spring; and (e) a battery for driving said displacement gauge.

2. A precise shear-stress measurement apparatus according to claim 1, wherein said piezoelectric element has a four-segment structure having a common electrode and at least two drive electrodes, and first and second voltages each having a triangular waveform are supplied to said drive electrodes, the first and second voltages having a phase difference of 180° therebetween.

3. A precise shear-stress measurement apparatus according to claim 1, wherein a member that provides said sample surface has a lens-like shape and is replaceable, and said member is held by a pair of springs disposed perpendicular to said sample surface and is horizontally moved by said piezoelectric element at a constant speed.

4. A precise shear-stress measurement apparatus according to claim 3, wherein said sample surface is a surface of a solid material such as glass or mica, or a chemically modified surface of the solid material.

5. A precise shear-stress measurement apparatus according to claim 1, wherein said capacitance-type displacement gauge is provided with a lock-in amplifier.

6. A precise shear-stress measurement apparatus comprising a spring disposed perpendicularly to a sample surface; a cylindrical piezoelectric element disposed perpendicularly to said sample surface and connected to said spring, said piezoelectric element being circumferentially divided into a plurality of pieces; means for driving said piezoelectric element; and a capacitance-type displacement gauge for detecting a horizontal displacement of said spring, wherein said measurement apparatus is assembled as an exchangeable unit.

7. A precise shear-stress measurement apparatus according to claim 6, wherein said precise shear-stress measurement apparatus is immersed into a liquid within a sealed container.

8. A precise shear-stress measurement apparatus according to claim 6, wherein said precise shear-stress measurement apparatus in the form of a unit is built into a surface-force measurement apparatus which comprises:

means for measuring the distance between a pair of sample surfaces; and means for changing the distance between the pair of sample surfaces.

9. A precise shear-stress measurement apparatus according to claim 8, wherein the distance between the pair of surfaces is determined through measurement of interference fringes using white light.

* * * * *